United States Patent
Frank et al.

(10) Patent No.: US 6,445,765 B1
(45) Date of Patent: Sep. 3, 2002

(54) X-RAY DETECTING APPARATUS

(75) Inventors: Andreas Frank, Alsfeld-Leusel; Patricia Schall, Weiterstadt; Georg Geus, Wiesbaden, all of (DE)

(73) Assignee: Heimann Systems GmbH, Wiesbaden (DE)

( * ) Notice: Subject to any disclaimer, the term of this patent is extended or adjusted under 35 U.S.C. 154(b) by 0 days.

(21) Appl. No.: 09/659,040

(22) Filed: Sep. 11, 2000

(51) Int. Cl.⁷ ................................. A61B 6/00
(52) U.S. Cl. .................... 378/56; 378/54; 378/98.8; 378/98.9
(58) Field of Search ............... 378/53, 54, 57, 378/88, 5, 19, 56, 98.8, 98.9

(56) References Cited

U.S. PATENT DOCUMENTS

| | | | |
|---|---|---|---|
| 4,626,688 A | | 12/1986 | Barnes ............... 250/361 R |
| 5,138,167 A | * | 8/1992 | Barnes ................. 378/156 |
| 5,216,252 A | * | 6/1993 | Boone et al. ............ 250/486.1 |
| 5,440,129 A | * | 8/1995 | Schmidt ............... 250/366 |
| 5,518,658 A | * | 5/1996 | Rossner ............... 252/301.4 |
| 5,562,860 A | * | 10/1996 | Grabmaier et al. .... 262/301.45 |
| 5,841,832 A | * | 11/1998 | Mazess et al. ............ 378/56 |

FOREIGN PATENT DOCUMENTS

| DE | 44 02 258 A1 | 7/1995 |
|---|---|---|
| DE | 44 27 021 A1 | 2/1996 |

\* cited by examiner

Primary Examiner—David P. Porta
Assistant Examiner—Therese Barber
(74) Attorney, Agent, or Firm—Birch, Stewart, Kolasch & Birch, LLP

(57) ABSTRACT

The detector materials (8, 9) of a low energy detector (5) and a high energy detector (6) are coordinated with one another to permit better separation of lower and higher energy fractions of polychromatic X-ray (X') radiation, and consequently, create a better determination of a material of an object through which the X-rays are passed. Thus, a negligible persistence in comparison with the integration time between two detector readings is achieved.

15 Claims, 1 Drawing Sheet

X-RAY DETECTING APPARATUS

BACKGROUND OF THE INVENTION

1. Field of the Invention

The present invention relates to an X-ray detecting apparatus, in particular, a detector for determining a type of material of an object, through which X-rays are passed.

2. Related Art

To determine the type of material of an object through which X-rays are passed, there are known detector arrangements consisting of a plurality of detectors, mainly arranged in pairs. Each pair of detectors consists of two radiation detectors, which are arranged in succession and are penetrated in succession by X-ray quanta of a radiation source, with the front detector having a lower absorption than the rear detector, especially at higher energy levels; low energy X-ray quanta are absorbed almost completely in the low energy detector positioned in front. Higher energy X-ray quanta pass through the low energy detector with almost no interaction and are absorbed in the high-energy detector at the rear. The front detector may have a lower thickness than the rear detector. In addition, the two detectors may also have different chemical compositions and densities.

With such an arrangement, a separation of X-rays into individual energy ranges is achieved, so it is possible to determine the material type of the components of the object through which the X-rays are passed. The radiation detectors consist, for example, of solid-state scintillators in combination with semiconductor photodiodes. These solid-state luminescent materials (solid-state scintillators) convert X-rays into visible radiation, for example, which is then converted to a current signal by photodiodes. The current signal is proportional to the intensity of the X-rays absorbed.

Such an arrangement for detecting X-rays is disclosed in U.S. Pat. No. 4,626,688, where the individual energy ranges of the X-rays penetrate through an object having components and are attenuated. Polycrystalline phosphors have been proposed as detector materials, consisting of elements with atomic numbers in the range of 39 to 57 in the case of low energy detectors, and elements with atomic numbers in the range of 56 to 83 for high-energy detectors. The thickness of individual detectors at which good scintillation is guaranteed is determined as a function of these atomic numbers. A filter material is placed between the two detectors to achieve better separation of the two energy ranges.

One disadvantage of this arrangement is that it is very difficult to produce these phosphors with a homogeneous mass distribution in comparison with known single crystals having a homogeneous thickness. In addition, these phosphors in comparison with single crystals often have a reduced efficiency with respect to conversion of X-rays to light. This is due to the fact that some of the scintillation light generated is dispersed and/or absorbed on the phosphor particles within the phosphor layer. Consequently, phosphor layers supply a signal having a smaller signal-to-noise ratio than the signal of many single crystal scintillators.

Another disadvantage is based on the fact that with detector materials having an atomic number of approximately 50, the K absorption edge of the corresponding element in the range of 30 keV or more. If the low energy detector contains a material of such an element, the unwanted interaction of high energy X-ray quanta with energies above 50 keV in the low energy detector increases, with the main portion of the X-ray spectrum which is absorbed in the low energy detector being shifted toward the higher X-ray spectrum, thus reducing the quality of the separation of the two energy ranges.

German Patent 44 02 258 A1 describes a detector for detection of high-energy radiation, consisting of hot-pressed luminescent material and a photodiode or a photomultiplier. This luminescent material, which is also known as pressed ceramic, has good scintillation properties. The high energy X-rays are absorbed in the luminescent material, emitting as a result of this absorption visible light which is detected by the photodiode (photosensitive element). The luminescent material disclosed here is based on elements of a rare earth oxysulfide and has a low persistence.

German Patent 44 27 021 A1 discloses such a detector for detection of high-energy radiation, its detector material also containing additional doping. Such detectors are used in X-ray computer tomography.

SUMMARY OF THE INVENTION

The object of this invention is to provide a detector arrangement which will permit a better separation of the low energy components of a polychromatic X-ray from the high-energy components, and consequently, to create a better determination of a material type of an object through which the X-rays are passed.

The idea on which the present invention is based is to obtain a better energy separation through a coordinated choice of materials of a low energy detector and a high-energy detector. In the case of the low energy detector material, according to the present invention, a material is provided which has a low self-absorption of the scintillator light generated and a spectrum of the scintillation light adapted to the spectral sensitivity of the photodiode, as well as an advantageous chemical composition in addition to having a high efficiency in conversion of X-rays into light. Therefore, the detector material of a low energy detector has elements with atomic numbers in the range of 30 to 40. The thickness of the low energy detector is selected so that the low energy X-ray quanta are absorbed almost completely, but high-energy X-ray quanta with energy of more than 50 keV, for example, mostly pass through the low energy detector. The required great homogeneity of the thickness can be achieved by surface machining, such as polishing or lapping, for example. Advantageous embodiments of these low energy detectors are resistant to moisture and temperature fluctuations. Zinc selenide doped with tellurium has these properties in particular.

The high-energy detector is preferably made of a dense material consisting of elements with large atomic numbers in the range of 56 to 83, so that this detector can be made as thin as possible. This detector material is preferably a ceramic gadolinium oxysulfide doped with at least one rare earth element.

Because of the coordinated choice of materials of the low energy detector and the high-energy detector, the detector arrangement has a low persistence and is thus definitely improved in comparison with the energy-selective detector arrangements known in the past.

In the case of a linear or flat arrangement of such detector pairs, there is the effect that scintillation light is propagated in the detector material and is detected in adjacent photodiodes. This so-called optical crosstalk leads to reduced contrast in the X-ray image and also falsifies the determination of the material. This effect increases greatly with an increase in thickness of the material of the detector and reduced self-absorption of the scintillation light. To counteract this effect, the detector is segmented into individual pixels and separated by a reflective layer of titanium oxide or aluminum oxide, for example. This separation takes place with both the low energy detector and the high-energy detector.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The present invention will become more fully understood from the detailed description given hereinbelow and the accompanying drawings, which are given by way of illustration only, and thus are not limitative of the present invention, and wherein.

DETAILED DESCRIPTION OF THE PREFERRED EMBODIMENTS

Figure 1:
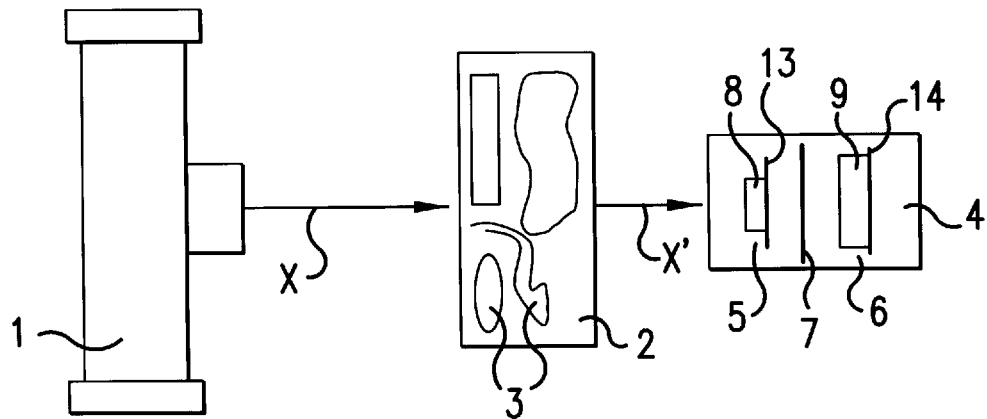
FIG. 1 illustrates an arrangement for detecting X-rays with two detectors.

FIG. 1 illustrates an X-ray generator 1 where an X-ray X is generated having an energy range of 10 to 500 keV, preferably up to 140 keV, and is reflected. This X-ray X penetrates through an object 2 located in the path of the beam. The object 2 has various components 3, which may be made of different materials. Due to the different absorption properties of the individual materials of these components 3 in the path of the beam, an X-ray X' with an altered spectral composition and a reduced intensity strikes a detector arrangement 4, which is illustrated in the figure in cross-section.

Figure 2:
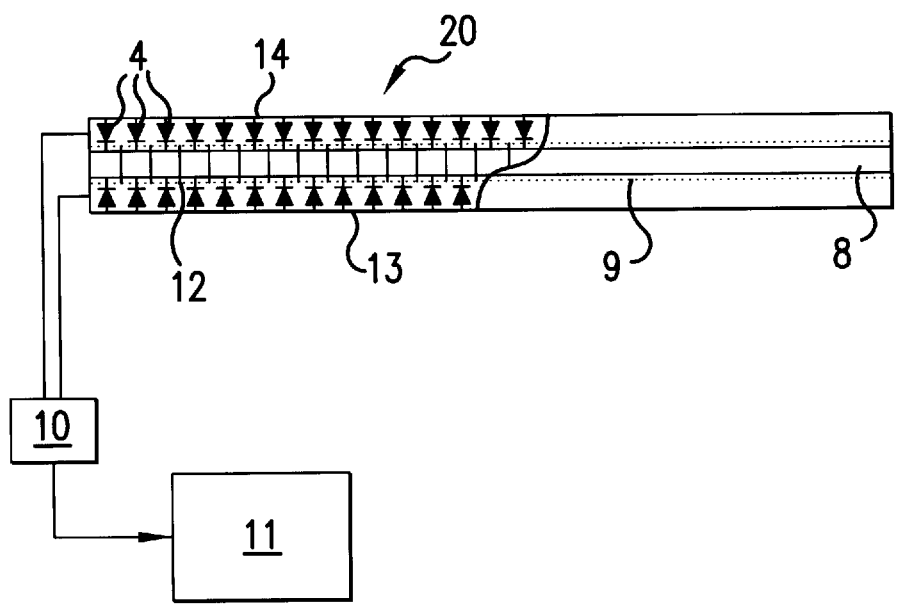
FIG. 2 illustrates a detector line consisting of detectors shown in FIG. 1, with an analyzer unit and a monitor.

A plurality of detectors of the same design of detector arrangement 4 preferably form a detector line 20, as illustrated in FIG. 2 (to be explained below). The individual detector arrangement 4, designed here as a detector pair, is composed of a first front detector 5 and a second rear detector 6. The first detector 5 is a low energy detector and absorbs mainly the low energy range or part of the attenuated X-ray X', while the second detector 6 is a high energy detector and absorbs the high energy range or part of the attenuated X-ray X'. Depending on the type of material and the thickness of the material of components 3, X-ray X' strikes the detector arrangement 4 (or the detector line 20) in attenuated form, generating signals characteristic of the absorption properties of the materials of components 3 in a known manner. These are sent as individual signals to an analyzer unit 10 and analyzed, and may also be displayed as an image on a monitor 11 (FIG. 2).

To obtain more specific information about a material in automated determination of the type of material, it must be possible to separate the energies or energy ranges analyzed. This is accomplished through a purposeful choice of detector material 8 of the low energy detector 5 in coordination with detector material 9 of the high-energy detector 6.

This detector 6 is preferably made of a pressed ceramic containing at least one element having an atomic number of more than 60, such as gadolinium oxysulfide $Gd_2O_2S$ (SE) doped with at least one rare earth element SE selected from, for example, Ce, Pr and Tb. The thickness of detector material 9 of the detector 6 preferably amounts to 1.0 to 2.0 mm. A coordinated detector material 8 for the low energy detector 5 used on this detector material 9 is preferably made of a scintillation material containing at least one element with an atomic number of 30 to 40, but not containing any element with a larger atomic number. It has been found here that good separation of the energy ranges can be achieved with a detector material 8 made of zinc selenide with tellurium doping ZnSe (Te). This zinc selenide was used in a thickness of 0.2 to 1.0 mm. Other advantages of this combination of materials include a lack of sensitivity to moisture and the fact that the emission wavelengths of the scintillation light are adapted to the spectral sensitivity of traditional photodiodes.

This controlled choice of detector material 8 for the low energy detector 5, by taking into account the detector material 9 for the high energy detector 6, also permits controlled use of coordinated low-persistence scintillation materials and detector materials 8, 9 for the low energy detector 5 as well as the high energy detector 6. Zinc selenide, in particular, as well as gadolinium oxysulfide each have a short persistence, each being smaller than the period of time between two detector readings. Consequently, more relevant measurement results and displays with a sharp contour are achieved and displayed. To do so, the attenuated X-rays X' are converted to visible radiation in detector layers 8, 9 and then converted by semiconductor photodiodes 13, 14, which correspond to detector layers 8, 9, into a current signal which is then sent for analysis to analyzer unit 10 of a computer unit (not shown) of an X-ray testing device or system.

In the case of a linear or flat arrangement of detector arrangement 4 to this detector line 20, the detector or scintillation material 8, 9 is segmented into individual pixels to avoid the known phenomenon of optical crosstalk between the side-by-side detector arrangements 4. The separation is accomplished by a reflective layer 12, which consists of titanium oxide or aluminum oxide, for example, and is introduced between the segmented pixels.

For further separation of the energies or energy ranges of the attenuated X-ray X', a filter 7 such as that illustrated in FIG. 1 may be placed between the two detectors 5 and 6. This filter is preferably made of copper and has a thickness of 0.2 to 1.0 mm, so that low energy components remaining in X-ray X' after passing through the detector 5 are absorbed.

This detector arrangement 4 may be integrated into an X-ray apparatus (not shown here) for nondestructive materials testing, for food testing and for inspection of baggage and freight.

It is self-evident that changes are possible within the scope of the inventive idea presented here. For example, detector arrangement 4 is not limited to two detectors.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A detector arrangement for detecting X-rays, comprising at least one low energy detector, and at least one high energy detector arranged downstream, where individual energy ranges of the X-ray are emitted at the same time on an object through which X-rays are passed and are attenuated in the process, wherein the low energy detector has as a detector material a scintillator comprising at least one element with an atomic number of 30 to 40, but not containing any element having a larger atomic number, said detector material being coordinated with a detector material of the high energy detector, and the latter detector material is a ceramic scintillator containing at least one element with an atomic number greater than 60.

2. The detector arrangement according to claim 1, wherein the scintillator of the low energy detector is a single crystal.

3. The detector arrangement according to claim 1, wherein the detector material of the low energy detector is zinc selenide doped with tellurium (ZnSe(Te)).

4. The detector arrangement according claim 1, wherein the detector material of the low energy detector has a thickness of 0.2 to 1.0 mm.

5. The detector arrangement according claim 1, wherein the detector material of the high energy detector is ceramic gadolinium oxysulfide $Gd_2O_2S$ doped with at least one rare earth element selected from the group consisting of Ce, Pr and Tb.

6. The detector arrangement according to claim 5, wherein the detector material of the high energy detector has a thickness of 1.0 to 2.0 mm.

7. The detector arrangement according to claim 1, wherein the low energy detector or the high-energy detector or both are separated into individual segments by reflective layers.

8. The detector arrangement according to claim 7, wherein the reflective layers are titanium oxide.

9. The detector arrangement according to claim 7, wherein the reflective layers are aluminum oxide.

10. The detector arrangement according to claim 1, wherein the detector material corresponds to respective semiconductor photodiodes, whereby an attenuated X-ray (X') is converted to visible radiation and then to an electric current signal.

11. The detector arrangement according to claim 1, wherein a filter is introduced between the low energy detector and the high-energy detector.

12. The detector arrangement according to claim 11, wherein the filter comprises copper.

13. The detector arrangement according to claim 11, wherein the filter has a thickness of 0.2–1.0 mm.

14. The detector arrangement according to claim 1, wherein X-rays incident on the object have an energy range of 10 to 500 keV.

15. A detector arrangement for detecting X-rays, comprising:
   at least one low energy detector; and
   at least one high energy detector arranged downstream, where individual energy ranges of the X-ray are emitted at the same time on an object through which X-rays are passed and are attenuated in the process, wherein the low energy detector has as a detector material a scintillator comprising zinc selenide doped with tellurium (ZnSe(Te)), but not containing any element having a larger atomic number, said detector material being coordinated with a detector material of the high energy detector, and the latter detector material is a ceramic scintillator containing at least one element with an atomic number greater than 60.

* * * * *